(12) United States Patent
Zambaux

(10) Patent No.: US 7,797,911 B2
(45) Date of Patent: Sep. 21, 2010

(54) STERILE, PYROGEN-FREE, POLYMERIC FILM-BASED HEATING BAG

(75) Inventor: Jean-Pascal Zambaux, Riom (FR)

(73) Assignee: Advanced Technology Materials, Inc., Danbury, CT (US)

(*) Notice: Subject to any disclaimer, the term of this patent is extended or adjusted under 35 U.S.C. 154(b) by 889 days.

(21) Appl. No.: 11/594,604

(22) Filed: Nov. 8, 2006

(65) Prior Publication Data

US 2007/0054076 A1 Mar. 8, 2007

Related U.S. Application Data

(62) Division of application No. 10/658,034, filed on Sep. 9, 2003, now abandoned.

(51) Int. Cl.
B65B 55/02 (2006.01)
(52) U.S. Cl. ............. 53/425; 53/477; 428/34.1; 428/35.2; 428/421; 428/422; 156/308.4; 156/731
(58) Field of Classification Search ............ 53/425, 53/477; 156/73.1, 73.3, 308.4; 428/35.2, 428/34.1, 421, 422
See application file for complete search history.

(56) References Cited

U.S. PATENT DOCUMENTS

| 3,061,087 A | 10/1962 | Scrivens et al. |
| 3,093,242 A | 6/1963 | Huyck et al. |
| 3,229,813 A | 1/1966 | Crowe, Jr. et al. |
| 3,460,742 A | 8/1969 | Langdon |
| 3,575,225 A | 4/1971 | Muheim |
| 3,604,616 A | 9/1971 | Greif |
| 3,991,881 A | 11/1976 | Augurt |
| 4,055,672 A | 10/1977 | Hirsch et al. |
| 4,119,267 A | 10/1978 | Kydonieus |
| 4,121,714 A | 10/1978 | Daly et al. |
| 4,212,299 A | 7/1980 | Yokokoji et al. |
| 4,320,224 A | 3/1982 | Rose et al. |

(Continued)

FOREIGN PATENT DOCUMENTS

DE 39 15 252 A1 11/1990

(Continued)

OTHER PUBLICATIONS

Franks, Stephen, "Strength and Integrity—The basics of medical package testing", "Found on-line at http://www.tmelectronics.com/Strength_and_Integrity.pdf", 2001, Publisher: TM Electronics, Inc.

Primary Examiner—Michael C Miggins
(74) Attorney, Agent, or Firm—Vincent K. Gustafson; Intellectual Property/Technology Law; David Shofi

(57) ABSTRACT

In one embodiment, there is provided a method for producing a sterilized and pyrogen-free bag for storing fluids. The method includes providing a bag comprised of polymeric film and heating the bag to at least approximately 253 degrees Celsius for at least approximately 30 minutes for sterilization and pyrogen removal. The polymeric film is a polymer selected from the group of poly(oxy-1,4-phenylene-oxy-1,4-phenylene-carbonyl-1,4-phenylene) (PEEK); polytetrafluoroethylene (PTFE); a perfluoroalkoxy (PFA) polymer; poly(tetrafluoroethylene-co-perfluoromethyl vinyl ether) (MFA); polyperfluoro(ethylene-co-propylene)(FEP); poly(ethylene-alt-chlorotrifluoroethylene) (ECTFE); poly(ethylene-co-tetrafluoroethylene) (ETFE); poly(vinylidene fluoride) (PDVF); tetrafluoroethylene-co-hexafluoropropylene-co-vinylidene fluoride terpolymer (THV); poly(bisphenol A-co-4-nitrophthalic anhydride-co-1,3-phenylenediamine) (PEI); poly(4-methyl-1-pentene) (PMP); and suitable mixtures thereof.

20 Claims, 3 Drawing Sheets

U.S. PATENT DOCUMENTS

| | | | |
|---|---|---|---|
| 4,407,872 A | 10/1983 | Horii | |
| 4,461,420 A | 7/1984 | Horvath | |
| 4,539,836 A | 9/1985 | Hester et al. | |
| 4,561,110 A * | 12/1985 | Herbert | 604/408 |
| 4,706,494 A | 11/1987 | Creed et al. | |
| 5,217,772 A | 6/1993 | Brown et al. | |
| 5,314,421 A | 5/1994 | Leuenberger | |
| 5,314,732 A | 5/1994 | Wiste | |
| 5,418,022 A | 5/1995 | Anderson et al. | |
| 5,459,978 A | 10/1995 | Weiss et al. | |
| 5,590,778 A | 1/1997 | Dutchik | |
| 5,591,468 A | 1/1997 | Stockley, III et al. | |
| 5,739,463 A | 4/1998 | Diaz et al. | |
| 5,770,301 A | 6/1998 | Murai et al. | |
| 5,830,547 A | 11/1998 | MacKenzie et al. | |
| 5,976,299 A | 11/1999 | Ivey | |
| 5,993,593 A | 11/1999 | Swartz et al. | |
| 6,065,597 A | 5/2000 | Pettersson et al. | |
| 6,094,361 A | 7/2000 | Batten, Jr. et al. | |
| 6,130,002 A | 10/2000 | Neumann et al. | |
| 6,251,489 B1 | 6/2001 | Weiss et al. | |
| 6,460,405 B1 | 10/2002 | Mayer et al. | |
| 6,513,366 B1 | 2/2003 | Stauffer | |
| 6,609,414 B2 | 8/2003 | Mayer et al. | |
| 6,786,933 B2 | 9/2004 | Merrill et al. | |
| 7,036,287 B1 | 5/2006 | Webb | |
| 7,067,616 B2 | 6/2006 | Alberg | |
| 7,160,590 B2 | 1/2007 | Vanhamel et al. | |
| 7,335,721 B2 | 2/2008 | Alberg | |
| 2002/0022682 A1 | 2/2002 | Wallace et al. | |
| 2003/0015021 A1 | 1/2003 | Mayer et al. | |
| 2005/0050854 A1 | 3/2005 | Zambaux | |
| 2005/0098457 A1 | 5/2005 | Van Hamel et al. | |

FOREIGN PATENT DOCUMENTS

| | | |
|---|---|---|
| DE | 198 17 548 A1 | 10/1999 |
| EP | 1 331 839 A1 | 7/2003 |
| GB | 2 001 006 A | 1/1979 |
| JP | 02-245228 A1 | 10/1990 |
| JP | 02245228 A1 | 10/1990 |
| JP | 2000-153874 A | 6/2000 |
| JP | 2000-203563 A | 7/2000 |
| WO | 03061958 A1 | 7/2003 |
| WO | 2005003189 A1 | 1/2005 |

* cited by examiner

STERILE, PYROGEN-FREE, POLYMERIC FILM-BASED HEATING BAG

CROSS-REFERENCE TO RELATED APPLICATION(S)

This application is related to and a divisional of application Ser. No. 10/658,034, filed on Sep. 9, 2003, and entitled "Sterile Pyrogen-Free Polymeric Film-Based Heating Bag", now abandoned.

TECHNICAL FIELD

This invention generally relates to a method of heating a bag. More particularly, the invention relates to a method for producing an essentially sterile, pyrogen-free, polymeric film-based heating bag. The polymeric film can include a polymer selected from the group of poly(oxy-1,4-phenylene-oxy-1,4-phenylene-carbonyl-1,4-phenylene) (PEEK); polytetrafluoroethylene (PTFE); a perfluoroalkoxy (PFA) polymer; poly(tetrafluoroethylene-co-perfluoromethyl vinyl ether) (MFA); polyperfluoro(ethylene-co-propylene) (FEP); poly(ethylene-alt-chlorotrifluoroethylene) (ECTFE); poly(ethylene-co-tetrafluoroethylene) (ETFE); poly(vinylidene fluoride) (PDVF); tetrafluoroethylene-co-hexafluoropropylene-co-vinylidene fluoride terpolymer (THV); ultra-high molecular weight polyethylene (UHMW PE); (poly(bisphenol A-co-4-nitrophthalic anhydride-co-1,3-phenylenediamine) (PEI); poly(4-methyl-1-pentene) (PMP); and suitable mixtures thereof.

BACKGROUND OF THE INVENTION

The storage of fluids and liquids that are essentially free of contaminants and bacteria is important across a number of different industries. For example, in the medical field, the storage of bodily fluids, such as blood, in containers that are free of pyrogen are important. In particular, pyrogen is a substance or agent that produces fever. Pyrogen may be present in containers that store bodily fluids. Accordingly, such containers may contaminate the bodily fluids stored therein with this pyrogen. A current requirement from a number of government agencies (including the Federal Drug Administration (FDA)) is that such containers are to be heated to at least 253 degrees Celsius for at least approximately 30 minutes to one hour (to remove pyrogen therefrom) prior to storage of the fluids.

A conventional approach is to use glass containers because such containers may withstand the required temperature. However, the use of glass containers can be problematic. In particular, the glass containers may break if dropped. Moreover, such containers, which cannot typically be reused in certain applications (storage of bodily fluids), are relatively expensive.

A typical application of storage of fluids that are to be sterilized and pyrogen free includes the transfer of blood from a first individual to a second individual. In particular, the blood is drawn from the first individual and stored in a glass container (that has been sterilized and free of pyrogen). Subsequently, the blood is transferred into the second individual. However, when glass containers are used in such an application, air is typically trapped in the glass container along with the blood. Therefore, when the blood is transferred into the second individual, if such transfer is not closely monitored, the air in the glass container can be transferred into the second individual as well. A conventional approach to preclude the introduction of the air into the second individual during the blood transfusion is to include an electronic monitoring. Accordingly, when the transfer of the blood is completed, the electronic monitoring detects that air is in the connector (coupling the glass container to the body). The electronic monitoring then closes a shutoff valve inside the connector to preclude the transfer of air from the glass container into the body. However, such equipment that allows for the electronic monitoring is relatively expensive and must be unique for each individual receiving a blood transfusion.

BRIEF SUMMARY OF THE INVENTION

There is provided a method for producing a sterilized and pyrogen-free bag for storing fluids. The method includes providing a bag comprised of polymeric film and heating the bag to at least approximately 253 degrees Celsius for at least approximately 30 minutes for sterilization and pyrogen removal. The polymeric film is a polymer selected from the group of poly(oxy-1,4-phenylene-oxy-1,4-phenylene-carbonyl-1,4-phenylene) (PEEK); polytetrafluoroethylene (PTFE); a perfluoroalkoxy (PFA) polymer; poly(tetrafluoroethylene-co-perfluoromethyl vinyl ether) (MFA); polyperfluoro(ethylene-co-propylene)(FEP); poly(ethylene-alt-chlorotrifluoroethylene) (ECTFE); poly(ethylene-co-tetrafluoroethylene) (ETFE); poly(vinylidene fluoride) (PDVF); tetrafluoroethylene-co-hexafluoropropylene-co-vinylidene fluoride terpolymer (THV); poly(bisphenol A-co-4-nitrophthalic anhydride-co-1,3-phenylenediamine) (PEI); poly(4-methyl-1-pentene) (PMP); and suitable mixtures thereof.

BRIEF DESCRIPTION OF THE DRAWINGS

Embodiments of the invention may be best understood by referring to the following description and accompanying drawings which illustrate such embodiments. The numbering scheme for the Figures included herein are such that the leading number for a given reference number in a Figure is associated with the number of the Figure. For example, a polymeric film-based bag 100 can be located in FIG. 1. However, reference numbers are the same for those elements that are the same across different Figures. In the drawings.

DETAILED DESCRIPTION

Figure 1A:
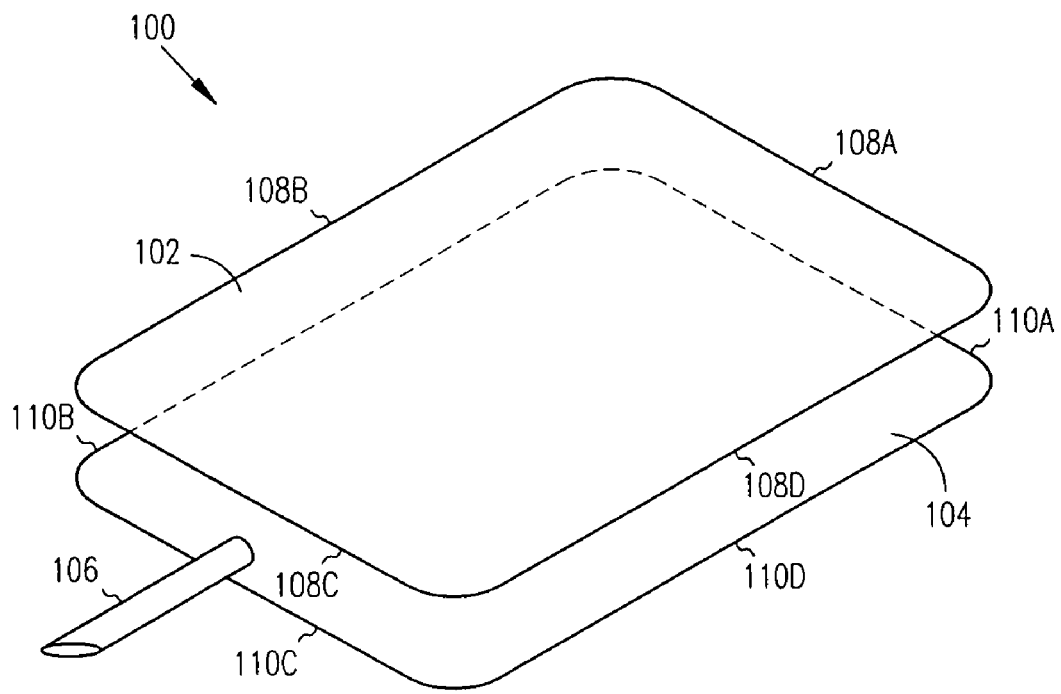
FIG. 1A illustrates parts of a bag comprised of a polymeric film, according to one embodiment of the invention.

Methods, apparatuses and systems for different embodiments for an essentially sterile, pyrogen-free, polymeric film-based heating bag are described. References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein, "polymeric" or "polymer" refers to poly (oxy-1,4-phenylene-oxy-1,4-phenylene-carbonyl-1,4-phenylene) (PEEK); polytetrafluoroethylene (PTFE); a perfluoroalkoxy (PFA) polymer; poly(tetrafluoroethylene-co-perfluoromethyl vinyl ether) (MFA); polyperfluoro(ethylene-co-propylene) (FEP); poly(ethylene-alt-chlorotrifluoroethylene) (ECTFE); poly(ethylene-co-tetrafluoroethylene) (ETFE); poly(vinylidene fluoride) (PDVF); tetrafluoroethylene-co-hexafluoropropyl-ene-co-vinylidene fluoride terpolymer (THV); (poly(bisphenol A-co-4-nitrophthalic anhydride-co-1,3-phenylenediamine) (PEI); poly(4-methyl-1-pentene) (PMP); and suitable mixtures thereof.

Poly(oxy-1,4-phenylene-oxy-1,4-phenylene-carbonyl-1, 4-phenylene) (PEEK) is a non-fluorinated polymer that has a repeat unit that comprises oxy-1,4-phenylene-oxy-1,4-phenylene-carbonyl-1,4-phenylene. PEEK is commercially available from Victrex (http://www.victrex.com/us/) and is shown below:

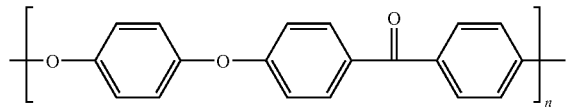

Polytetrafluoroethylene (PTFE) is a fluorinated polymer in which the film typically has a thickness of about 0.0115 inches to about 0.25 inches (as commercially sold). PTFE is commercially available from Saint-Gobain Performance Plastics and Aldrich Chemicals (Aldrich entry #43,093-5), has a CAS Reg. No. of #9002-84-0, and is shown below:

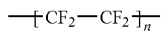

A perfluoroalkoxy (PFA) polymer resin is a fluorinated polymer in which the film typically has a thickness of about 0.0005 inches to about 0.030 inches (as commercially sold). PFAs are commercially available from Saint-Gobain Performance Plastics and are shown below:

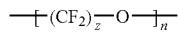

Poly(tetrafluoroethylene-co-perfluoromethyl vinyl ether) (MFA) is a fluorinated polymer in which the film typically has a thickness of about 0.0005 inches to about 0.03 inches (as commercially sold). MFA is commercially available from Saint-Gobain Plastics and is shown below:

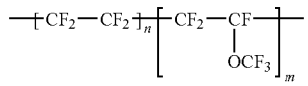

Polyperfluoro(ethylene-co-propylene) (FEP) is a fluorinated polymer commercially available from Saint-Gobain Plastics and is shown below:

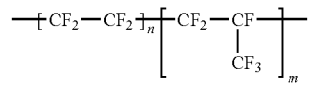

Poly(ethylene-alt-chlorotrifluoroethylene) (ECTFE) or ethylene-chlorotrifluoroethylene is a fluorinated polymer that is commercially available from Saint-Gobain Performance Plastics and Aldrich (Aldrich entry #42,721-7) and has a CAS Reg. No. 25101-45-5. ECTFE is shown below:

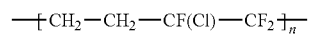

Poly(ethylene-co-tetrafluoroethylene) (ETFE) or ethylene-tetrafluoroethylene is a fluorinated polymer that is commercially available from Saint-Gobain Performance Plastics and Aldrich (Aldrich entry #42,719-5) and has a CAS Reg. No. 25038-71-5. The structure of ETFE is shown below:

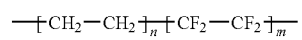

Poly(vinylidene fluoride) (PVDF) is a fluorinated polymer that is commercially available from Saint-Gobain Performance Plastics and Aldrich (Aldrich entry #42,715-2) and has a CAS Reg. No. 24937-79-9. The structure of PVDF is shown below:

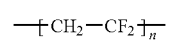

and has an average molecular weight of about 180,000 g/mol or about 275,000 g/mol from gas permeation chromatography (GPC); or an average molecular weight of up to about 534,000 from Aldrich.

Tetrafluoroethylene-co-hexafluoropropylene-co-vinylidene fluoride terpolymer (THV) or tetrafluoroethylene-hexafluoropropylene-vinylidene fluoride terpolymer is a fluorinated polymer that is commercially available from Saint-Gobain Performance Plastics and Aldrich (Aldrich entry #45, 458-3). THV has a CAS Reg. No. of 54675-89-7 and is shown below:

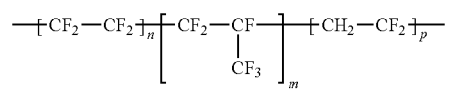

Poly(bisphenol A-co-4-nitrophthalic anhydride-co-1,3-phenylenediamine) (PEI) or polyether imide is a non-fluorinated polymer that is commercially available from Saint-Gobain Performance Plastics and Aldrich (Aldrich entry #43, 229-6) and has a CAS Reg. No. 61128-46-9. The structure of PEI is shown below:

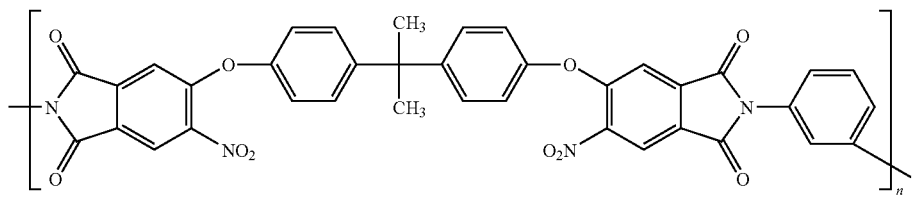

Poly(4-methyl-1-pentene) (PMP) or polymethyl pentene is commercially available from Saint-Gobain Performance Plastics and Aldrich (Aldrich entry #19,099-3) and is shown below:

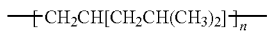

In one embodiment of the invention, the polymer or polymeric film can include PEEK. In another embodiment of the present invention, the polymer or polymeric film can include a fluorinated polymer described above. In another embodiment of the present invention, the polymer or polymeric film can include a non-fluorinated polymer described above.

A number of figures show diagrams of systems and apparatuses of a polymeric film-based bag, in accordance with embodiments of the invention. A number of figures show flow diagrams illustrating operations for manufacture and use of a polymeric film-based bag (that is essentially sterile and pyrogen free). The operations of the flow diagrams will be described with references to the systems/apparatus shown in the diagrams. However, it should be understood that the operations of the flow diagrams could be performed by embodiments of systems and apparatus other than those discussed with reference to the diagrams, and embodiments discussed with reference to the systems/apparatus could perform operations different than those discussed with reference to the flow diagrams.

FIG. 1A illustrates parts of a bag comprised of a polymeric film, according to one embodiment of the invention. FIG. 1A illustrates a polymeric film-based bag 100 that includes a first polymeric film 102, a second polymeric film 104 and a connector 106. In one embodiment, the connector 106 is made of polymeric. The first polymeric film 102 has an edge 108A, an edge 108B, an edge 108C and an edge 108D. The second polymeric film 104 has an edge 110A, an edge 110B, an edge 110C and an edge 110D. As shown, the connector 106 is approximately perpendicular to the side 108C and the side 110C. In an embodiment, the thickness of the first polymeric film 102 and/or the thickness of the second polymeric film 104 may be in a range of approximately 15 to 50 microns.

In one embodiment, the first polymeric film 102 and/or the second polymeric film 104 has a viscosity in a range such that the film is of a pharmaceutical grade and may reach mechanical constraints regarding the application. For example, the first polymeric film 102 and/or the second polymeric film 104 may be of BC3-WH type.

Figure 1B:
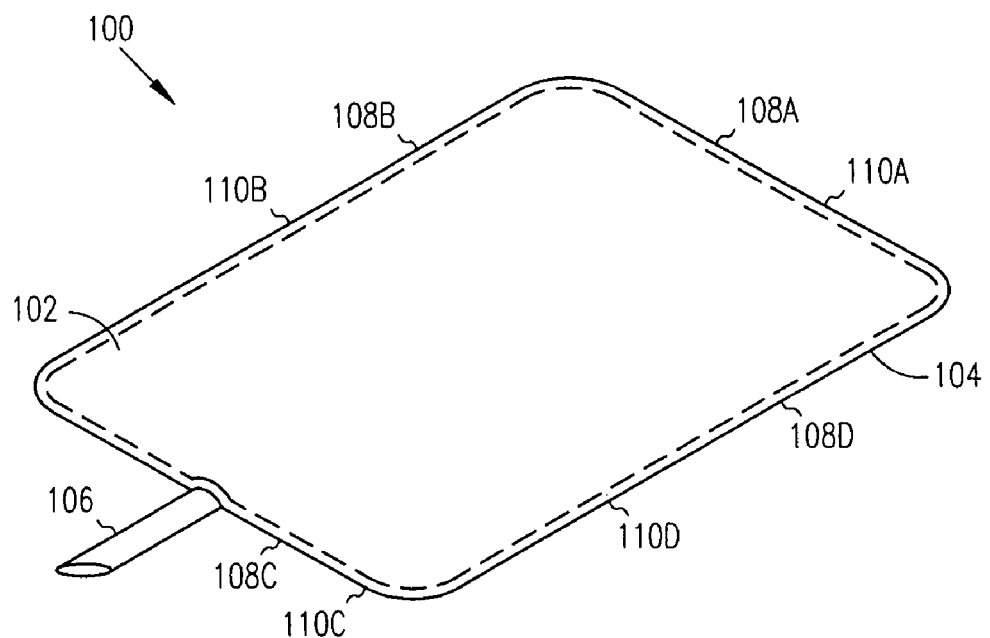
FIG. 1B illustrates a manufactured bag comprised of a polymeric film, according to one embodiment of the invention.

FIG. 1B illustrates a manufactured bag comprised of polymeric film, according to one embodiment of the invention. As shown, FIG. 1B illustrates the parts illustrated in FIG. 1A that have been coupled together to form the polymeric film-based bag 100. The edge 108A of the first polymeric film 102 is coupled to the edge 110A of the second polymeric film 104. The edge 108B of the first polymeric film 102 is coupled to the edge 110B of the second polymeric film 104. The edge 108C of the first polymeric film 102 is coupled to the edge 110C of the second polymeric film 104. The edge 108D of the first polymeric film 102 is coupled to the edge 10D of the second polymeric film 104. Accordingly, the connector 106 is between the edge 108C and the edge 110C after the edge 108C is coupled to the edge 110C.

Figure 2:
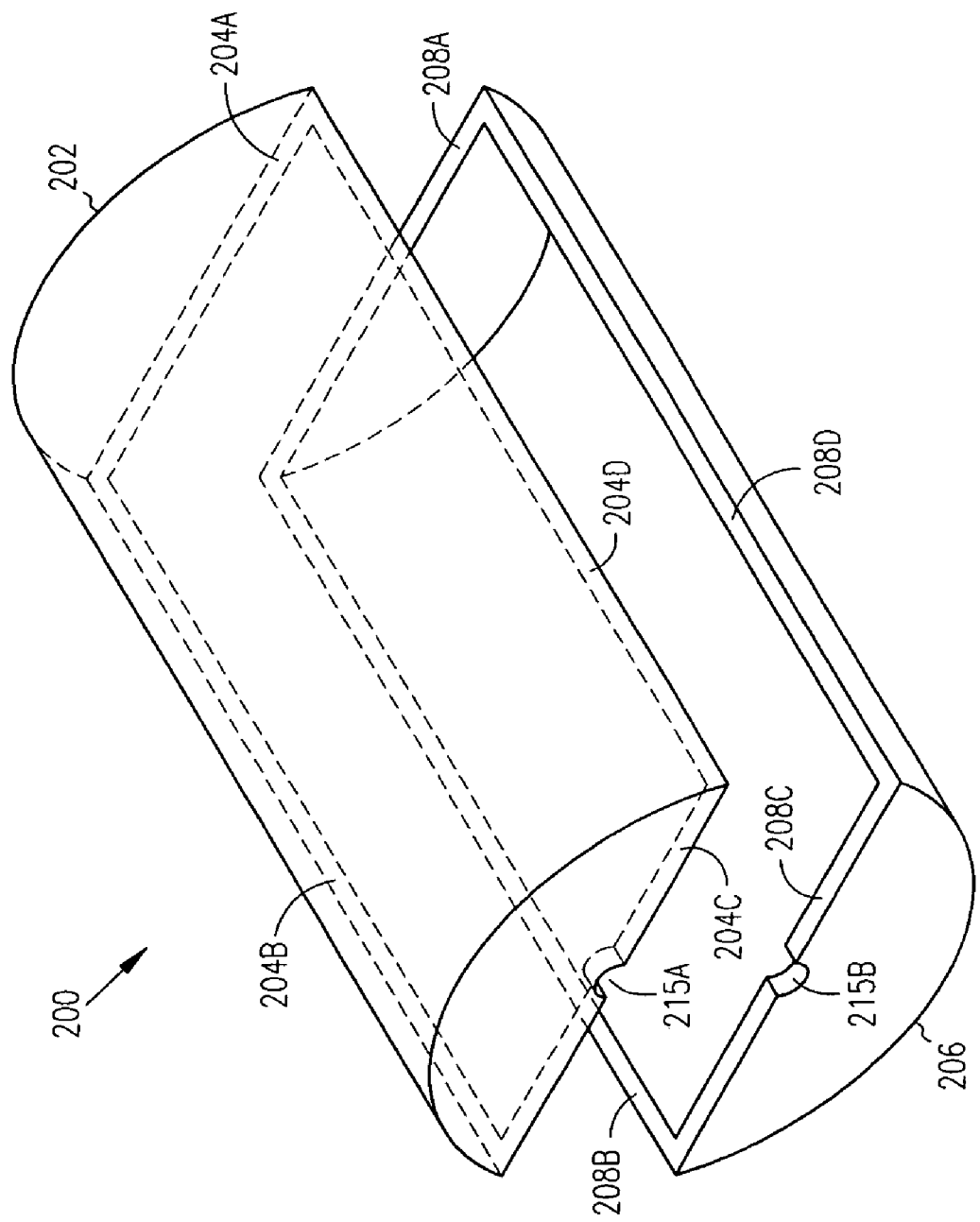
FIG. 2 illustrates an apparatus for manufacturing a bag comprised of a polymeric film, according to one embodiment of the invention.

In one embodiment, the edges 108A-108D are coupled to the edges 110A-110D, respectively, through a welding process. In one such embodiment, the edges 108A-108D are welded to the edges 110A-110D by heating such edges to a predefined temperature and pressing the edges together. In one embodiment, the predefined temperature is at least approximately 3300 Celsius. FIG. 2 illustrates an apparatus for manufacturing a bag comprised of a polymeric film, according to one embodiment of the invention. As shown, an apparatus 200 includes a first press 202 and a second press 206. The first press 202 includes a press edge 204A, a press edge 204B, a press edge 204C and a press edge 204D. The second press 206 includes a press edge 208A, a press edge 208B, a press edge 208C and a press edge 208D. The remaining part of the first press 202 (that is interior to the press edge 204A, the press edge 204B, the press edge 204C and the press edge 204D) is recessed. The remaining part of the first press 202 (that is interior to the press edge 208A, the press edge 208B, the press edge 208C and the press edge 208D) is recessed.

The press 202 includes a first slot 215A in the press edge 208C. The press 206 includes a second slot 215B. The first slot 215A and the second slot 215B allow for the placement of the connector 106 approximately perpendicular to the press edge 204C and the press edge 208C during the weld operation.

The first polymeric film 102 is placed in the first press 202 and the second polymeric film 104 is placed in the second press 206. The edge 108A is aligned with the press edge 204A. The edge 108B is aligned with the press edge 204B. The edge 108C is aligned with the press edge 204C. The edge 108D is aligned with the press edge 204D. The edge 110A is aligned with the press edge 208A. The edge 10B is aligned with the press edge 208B. The edge 110C is aligned with the press edge 208C. The edge 110D is aligned with the press edge 208D. In operation, the first press 202 is pressed into the second press 206. Accordingly, the edges 108A-108D are pressed to the edges 110A-110D, respectively. However, the remaining part of the first polymeric film 102 and the remaining part of the second polymeric film 104 are not in contact with each other. In an embodiment, the press, edges 204A-204D and the press edges 208A-208D are heated to a predefined temperature. In one embodiment, the predefined temperature is at least approximately 330 degree. Celsius. In an embodiment, the press edges 204A-204D and the press edges 208A-208D comprise a covered liquid (e.g., an oil). Accordingly, the temperature is more homogenous across the press edges 204A-204D and the press edges 208A-208D.

Embodiments for the manufacture of the polymeric film-based bags are not limited to the weld operation illustrated in FIG. 2. For example, in an embodiment, the edges 108A-108D are coupled to the edges 110A-110D, respectively, through ultrasonic sealing.

Figure 3:
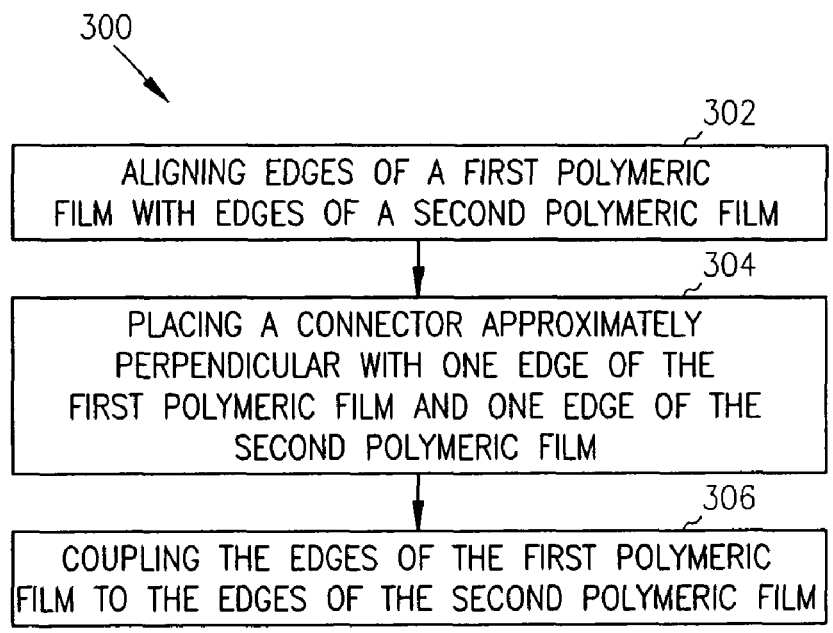
FIG. 3 illustrates a flow diagram for manufacturing a polymeric film-based bag, according to one embodiment of the invention.

One embodiment for the manufacturing of a polymeric film-based bag is now described. In particular, FIG. 3 illustrates a flow diagram for manufacturing a polymeric film-based bag, according to one embodiment of the invention.

In block 302 of the flow diagram 300, the edges of a first polymeric film are aligned with the edges of a second polymeric film. With reference to the embodiment of FIG. 1A, the edges 108A-108D are aligned with the edges 110A-110D, respectively. Control continues at block 304.

In block 304, a connector is placed approximately perpendicular with one edge of the first polymeric film and one edge of the second polymeric film. With reference to the embodiment of FIG. 1A, the connector 106 is placed approximately perpendicular to the edge 108C and the edge 110C. Control continues at block 306.

In block 306, the edges of the first polymeric film are coupled to the edges of the second polymeric film. With reference to the embodiment of FIG. 1B, the edges 108A-108D of the first polymeric film 102 are coupled to the edges 110A-110D of the second polymeric film 104. As described above, such coupling may be performed by a number of different operations, including a welding operation, ultrasonic sealing, etc. The operations for manufacturing a polymeric film-based bag are complete.

Figure 4:
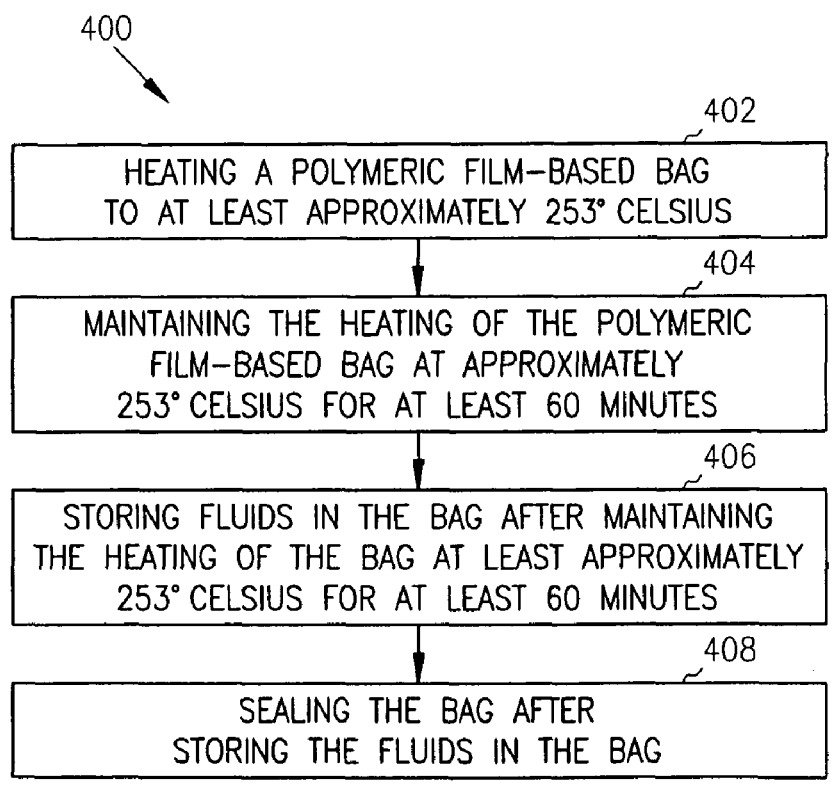
FIG. 4 illustrates a flow diagram for storing fluids in a polymeric film-based bag that is essentially sterile and pyrogen free, according to one embodiment of the invention.

One embodiment for using a polymeric film-based bag is now described. In particular, FIG. 4 illustrates a flow diagram for storing fluids in a polymeric film-based bag that is essentially sterile and pyrogen free, according to one embodiment of the invention. While described with reference to storage of fluids, embodiments of the invention are not so limited. For example, in other embodiments, different types of solids and gases may be stored therein. In an embodiment, the polymeric film-based bag may store different types of bodily fluids. For example, the fluids may be blood. In one embodiment, the fluids may be bodily fluids that include at least one of macrophages, B lymphocytes, cytotoxic T lymphocytes, plasma cells, helper cells, B lymphocytes, antibodies, erythrocytes, leukocytes, red blood cells, white blood cells, and platelets. In one embodiment, the fluids may be bodily fluids that include arterial blood, banked blood, cord blood, defibrinated blood, laky blood, oxalated blood, or whole blood.

In block 402 of the flow diagram 400, the polymeric film-based bag is heated to at least approximately 253 degrees Celsius. As described above, current requirements by the FDA for the sterilization and removal of pyrogen from containers, bags, etc include that the interior lining be heated to at least 253 degrees Celsius. In an alternative embodiment, the polymeric film-based bag is heated to a lesser or greater temperature depending on the application. Control continues at block 404.

In block 404, the heating of the polymeric film-based bag is maintained for at least 60 minutes. Current requirements by the FDA for the sterilization and removal of pyrogen from containers, bags, etc. include that the interior lining of such container, bags, etc. be heated to at least 253 degrees Celsius for at least 60 minutes. In an alternative embodiment, the heating of the polymeric film-based bag is maintained for a lesser or greater amount of time depending on the application. Control continues at block 406.

In block 406, fluids are stored in the polymeric film-based bag after heating the bag to at least 253 degrees Celsius for at least 60 minutes. Accordingly, fluids (essentially sterile and free of pyrogen) that are stored in this polymeric film-based bag stay essentially sterile and free of pyrogen. In other words, the polymeric film-based bag that has been treated as described above does not contaminate the fluids stored therein, because the inner lining of the bag is essentially sterile and free of pyrogen. With reference to FIG. 1B, the fluids are stored in the polymeric film-based bag through the connector 106. Control continues at block 408.

In block 408, the polymeric film-based bag is sealed after storing the fluids in the bag. With reference to FIG. 1B, the connector 106 is sealed after storing the fluids therein. In an embodiment, the polymeric film-based bag 100 may be incorporated into a kit. For example, the kit may include the polymeric film-based bag 100 (subsequent to sterilization and removal of pyrogen) along with packaging material and instructions or indicia located on the packaging material or inside the packaging material. In one such embodiment, fluids may be included in such a kit (stored either external or internal to the polymeric film-based bag 100).

Thus, methods, apparatuses and systems for an essentially sterile, pyrogen-free, polymeric film-based heating bag have been described. Although the present invention has been described with reference to specific exemplary embodiments, it will be evident that various modifications and changes may be made to these embodiments without departing from the broader spirit and scope of the invention. Therefore, the specification and drawings are to be regarded in an illustrative rather than a restrictive sense.

The invention claimed is:

1. A method for producing a sterilized and pyrogen-free bag for storing fluids, the method comprising: providing a bag comprised of polymeric film comprising a polymer selected from the group of poly(oxy-1,4-phenylene-oxy-1,4-phenylene-carbonyl-1,4-phenylene) (PEEK); polytetrafluoroethylene (PTFE); a perfluoroalkoxy (PFA) polymer; poly(tetrafluoroethylene-co-perfluoromethyl vinyl ether) (MFA); polyperfluoro(ethylene-co-propylene)(FEP); poly(ethylene-alt-chlorotrifluoroethylene) (ECTFE); poly(ethylene-co-tetrafluoroethylene) (ETFE); poly(vinylidene fluoride) (PDVF); tetrafluoroethylene-co-hexafluoropropylene-co-vinylidene fluoride terpolymer (THV); poly(bisphenol A-co-4-nitrophthalic anhydride-co-1,3-phenylenediamine) (PEI); poly(4-methyl-1-pentene)(PMP); and suitable mixtures thereof; and heating the bag to at least approximately 253 degrees Celsius for at least approximately 30 minutes for sterilization and pyrogen removal.

2. The method of claim 1, wherein the heating step includes the step of heating the bag to at least 253 degrees Celsius for at least approximately 60 minutes for sterilization and pyrogen removal.

3. The method of claim 1, wherein providing a bag comprised of polymeric film comprises providing a first polymeric film and a second polymeric film, wherein the first polymeric film and the second polymeric film each has a thickness of between about 15 microns and about 50 microns.

4. A sterilized and pyrogen-free bag for storing fluids made by the method of claim 1.

5. The bag of claim 4, wherein the polymeric film comprising a polymer selected from the group of poly(oxy-1,4-phenylene-oxy-1,4-phenylene-carbonyl-1,4-phenylene) (PEEK); poly(tetrafluoroethylene-co-perfluoromethyl vinyl ether) (MFA);
  polyperfluoro(ethylene-co-propylene) (FEP); poly(ethylene-co-tetrafluoroethylene) (ETFE);
  poly(vinylidene fluoride) (PDVF); tetrafluoroethylene-co-hexafluoropropylene-co-vinylidene fluoride terpolymer (THV); poly(bisphenol A-co-4-nitrophthalic anhydrideco-1,3-phenylenediamine) (PEI); poly(4-methyl-1-pentene) (PMP); and suitable mixtures thereof.

6. The method of claim 1, wherein providing a bag comprised of a polymeric film comprises: aligning edges of a first polymeric film and a second polymeric film; and coupling the edges of the first polymeric film to the edges of the second polymeric film.

7. The method of claim 6, and further comprising applying a covered liquid to the edges of the first polymeric film and the second polymeric film prior to coupling the edges of the first polymeric film to the edges of the second polymeric film.

8. The method of claim 6, wherein coupling the edges of the first polymeric film to the edges of the second polymeric film comprises welding the edges of the first polymeric film to the edges of the second polymeric film.

9. The method of claim 8, wherein welding the edges of the first polymeric film to the edges of the second polymeric film comprises heating the edges of the first polymeric film and the edges of the second polymeric film to a temperature of at least 330° Celsius.

10. The method of claim 9, wherein welding the edges of the first polymeric film to the edges of the second polymeric film comprises heating the edges of the first polymeric film and the second polymeric film and pressing the edges of the first polymeric film to the edges of the second polymeric film.

11. The method of claim 8, wherein welding the edges of the first polymeric film to the edges of the second polymeric film comprises using a first press and a second press.

12. The method of claim 6, wherein coupling the edges of the first polymeric film to the edges of the second polymeric film comprises ultrasonically sealing the edges of the first polymeric film to the edges of the second polymeric film.

13. The method of claim 6, and further comprising placing a connector approximately perpendicular with an edge of the first polymeric film and an edge of the second polymeric film.

14. The method of claim 13, wherein placing the connector approximately perpendicular with the edge of the first polymeric film and the edge of the second polymeric film comprises placing a connector comprised of polymeric material approximately perpendicular with the edge of the first polymeric film and the edge of the second polymeric film.

15. The method of claim 14, wherein the connector is comprised of a polymeric material.

16. The method of claim 15, wherein the polymeric material is selected from the group of poly(oxy-1,4-phenylene-oxy-1,4-phenylene-carbonyl-1,4-phenylene) (PEEK);
polytetrafluoroethylene (PTFE); a perfluoroalkoxy (PFA) polymer; poly(tetrafluoroethylene-co-perfluoromethyl vinyl ether) (MFA); polyperfluoro(ethylene-co-propylene)(FEP); poly(ethylene-alt-chlorotrifluoroethylene) (ECTFE); poly(ethylene-co-tetrafluoroethylene) (ETFE);
poly(vinylidene fluoride) (PDVF); tetrafluoroethylene-co-hexafluoropropylene-co-vinylidene fluoride terpolymer (THV); poly(bisphenol A-co-4-nitrophthalic anhydride-co-1,3-phenylenediamine)(PEI); poly(4-methyl-1-pentene)(PMP); and suitable mixtures thereof.

17. The method of claim 1, and further comprising dispensing a fluid into the bag.

18. The method of claim 17, wherein the fluid is a bodily fluid.

19. The method of claim 18, wherein the bodily fluid comprises at least one of the group consisting of: macrophages, B lymphocytes, cytotoxic T lymphocytes, plasma cells, helper cells, antibodies, erythrocytes, leukocytes, red blood cells, white blood cells, platelets, arterial blood, banked blood, cord blood, defibrinated blood, laky blood, oxalated blood, and whole blood.

20. The method of claim 17, and further comprising sealing the bag after storing the fluids in the bag.

* * * * *

UNITED STATES PATENT AND TRADEMARK OFFICE
CERTIFICATE OF CORRECTION

PATENT NO.         : 7,797,911 B2
APPLICATION NO.    : 11/594604
DATED              : September 21, 2010
INVENTOR(S)        : Jean-Pascal Zambaux It is certified that error appears in the above-identified patent and that said Letters Patent is hereby corrected as shown below:

Column 5, line 46, "polymeric." should be -- polymeric material. --.

Column 6, line 26, "3300 Celsius" should be -- 330° Celsius --.

Column 6, line 63, "330 degree. Celsius" should be -- 330 degrees Celsius --.

Signed and Sealed this

Twenty-first Day of December, 2010

David J. Kappos
*Director of the United States Patent and Trademark Office*